United States Patent [19]

Nenninger et al.

[11] 4,372,682
[45] Feb. 8, 1983

[54] MEDICAL TEST STRIP HOLDING DEVICE

[75] Inventors: Klaus Nenninger, Mannheim; Rainer Van Rijckevorsel, Brühl, both of Fed. Rep. of Germany

[73] Assignee: Clinicon Mannheim GmbH, Mannheim, Fed. Rep. of Germany

[21] Appl. No.: 244,988

[22] Filed: Mar. 18, 1981

[30] Foreign Application Priority Data

Mar. 22, 1980 [DE] Fed. Rep. of Germany ....... 3011223
Apr. 26, 1980 [DE] Fed. Rep. of Germany ....... 3016198

[51] Int. Cl.³ ............................................. G01N 21/13
[52] U.S. Cl. ................................................. 356/244
[58] Field of Search ....................... 350/86, 87, 88, 89, 350/90; 356/244

[56] References Cited

U.S. PATENT DOCUMENTS 3,738,730 6/1973 Binnings et al. .................. 350/90
4,248,498 2/1981 Georges ........................ 356/244 X Primary Examiner—John K. Corbin
Assistant Examiner—Matthew W. Koren
Attorney, Agent, or Firm—Sprung, Horn, Kramer & Woods

[57] ABSTRACT

A device for positioning and firmly holding a test strip for optical-medical measurements, comprising a housing with a reception opening having a stop at the inner end for the test strip and a window which is positioned opposite the test zone of the test strip when it is inserted into the reception opening and it lies against the stop. The device also comprises a pressing mechanism acting substantially at right-angles on the rear side of the test strip, which pressing mechanism, when inserting a test strip, is in a rest position remote from the test strip and, when the test strip is lying against the stop, is adapted to move into a pressing position in which it presses the test strip against the window, the pressing force of said pressing mechanism being substantially uniform in the positions corresponding to various thicknesses of the test strips.

12 Claims, 5 Drawing Figures

MEDICAL TEST STRIP HOLDING DEVICE

BACKGROUND OF THE INVENTION

The present invention relates to a device for positioning and firmly holding a test strip for optical-medical measurements, this device comprising a housing with a reception opening having a stop for the test strip on the inner end thereof and with a window which is positioned opposite the test zone of a test strip when the test strip is inserted into the reception opening and lies against the stop.

The precise positioning of a medical test strip in an appropriate evaluation device, usually a remission photometer, is of decisive importance for the exactitude of the evaluation of the test strip. On the one hand, it is, of course, important that the test strip lies, in the longitudinal direction, correctly below the window of the optical measuring device in order that only the appropriate test zone lies in the measurement area and not perhaps a part of the carrier material which would falsify the measurement result. On the other hand, it is extremely important that the distance between the optical measuring device and the surface of the test zone can be reproduced very precisely because, depending upon the construction of the optical system, the measured intensity enters into the result with the second to fourth power of the distance between the measurement field and the photoreceiver. In the case of a typical distance of 8 mm., a variation of the distance of only 0.1 mm. gives an error which is from 2.5 to 5%. Special difficulties arise from the fact that, if possible, test strips of different manufacture and for different medical parameters are to be measured with one apparatus. The thickness of these test strips can differ considerably in the region of the test zone.

In the case of a known apparatus, the test strips are introduced into a device provided therefor and firmly held in the measurement position by means of a leaf spring. In these devices, positioning is unsatisfactory not only in the longitudinal direction of the test strip but also with regard to the distance from the optical measurement system. It can happen relatively easily that when the test strip is inserted, it does not lie completely against the stop because the leaf spring has already exerted a considerable resistance to the insertion. On the other hand, it can also quite easily happen that the test strip, after insertion, is inadvertently pulled out of the apparatus to a small extent due to the fact that especially when the hands of the person operating the device are moist, which can frequently occur in a laboratory, the fingers stick somewhat to the test strip.

Furthermore, as has been recognized by applicants, positioning at right-angles to the surface of the test strip can also be insufficiently exact when test strips of varying thickness are to be measured. Thus, the tension of the leaf spring is, to a considerable extent, dependent upon the thickness of the test strip. The distance between the test zone and the optical measurement system also changes correspondingly to an extent which is unacceptable when a high degree of exactitude of the measurement is required.

Oftentimes the window in the reception opening has to be an open frame (e.g. to allow air to be in contact with the test piece) and in these cases the unsatisfactory results with known devices can easily be explained by the fact that different test zones are pressed into this frame to a different extent. However, as the present inventors found, also in apparatus with a firmly positioned closed window (e.g. by glass) the measuring results depend in most cases heavily on the strength of the force by which the test zone is pressed against the window.

SUMMARY OF THE INVENTION

Therefore, it is an object of the present invention to improve the positioning of test strips for optical-medical measurements so that a very accurate measurement result is achieved.

Thus, according to the present invention, there is provided a device for positioning and firmly holding a test strip for optical-medical measurements, the device comprising a housing with a reception opening having a stop for the test strip thereof and with a window which is positioned opposite the test zone of the test strip inserted into the reception opening and lying against the stop. The device also comprises a pressing mechanism acting substantially at right-angles on the rear side of the test strip. When inserting a test strip, the pressing mechanism is in a resting position remote from the test strip and, when the test strip is lying against the stop, the pressing mechanism is adapted to move into a pressing position in which it presses the test strip against the window, the pressing force of the pressing mechanism being substantially uniform in the positions corresponding to various thickness of the test strips.

Since the pressing mechanism used according to the present invention, is upon inserting a test strip, in a resting position remote therefrom, the test strip can be very easily introduced into the reception opening until it comes to rest against the stop. By appropriate means, the pressing mechanism is moved against the rear side of the test strip at the moment that it lies against the stop. For this purpose, for example, a photocell device can be used which is positioned in the region of the stop and which cooperates with an electromagnetic operation of the pressing mechanism. Furthermore, according to the present invention, the pressing mechanism is constructed in such a manner that its pressing force is substantially equal in the positions corresponding to different thicknesses of the test strips. When using the above-mentioned electromagnetic means, the coil of the electromagnet operating the pressing mechanism can be constructed, in known manner, so that the strength of the magnetic field is substantially constant in the range of movement of the coil core corresponding to the various possible test strip thicknesses so that a constant action of force also results. The operating device, by means of which the movement of the pressing mechanism from its resting position into its pressing position is initiated, can be constructed in various ways, for example, in the form of a manually operated release button. However, the operating device is preferably provided in the region of the stop so that it is moved by the inserted test strip, for example, the above-mentioned photocell device comprising a source of light and a photocell in the region of the stop for the test strip.

In comparison with the above-mentioned electromagnetic embodiment of the device according to the present invention, a mechanical means in advantageous because it does not require a supplementary source of energy. Preferred embodiments of such mechanical means are described hereinafter and are also referred to in the claims.

A spring mechanism is preferably used in order to produce the force necessary for the pressing mechanism. It is in positive connection, via force transmitting means, with the pressing mechanism, with the force transmission preferably being such that the transmission ratio of the force transmission and the force of the spring mechanism changing substantially reciprocally in the range of movement corresponding to various test strip thicknesses. The spring mechanism is preferably a mechanical spring, for example, a spiral or coil spring. However, a pneumatic piston-cylinder arrangement can, for example, also be used equally advantageously. Such spring mechanisms normally have a force which is dependent upon their degree of tension. This is, as mentioned above, unfavorable in the case of direct force transmission to the pressing mechanism because the positioning of the test strip in a direction at right-angles to the thickness of the test strip is thereby different if test strips of differing thickness are employed. The force transmission used according to the present invention can, for example, be constructed in the form of a cam plate upon which the spring mechanism acts at a definite angle via a roller. In such a case, the angle between the direction of action of the spring mechanism and the effective surface of the cam plate determines the force transmission. It is, therefore, readily possible to make the curve of the cam plate such that its force transmission changes, according to the present invention, reciprocally with respect to the change of the spring force.

According to a further preferred embodiment of the present invention, the range of movement of the pressing mechanism includes an apex: on the side of its range of movement proximal to the test strip, a force acts upon the pressing mechanism towards the test strip, whereas on the side of the range of movement remote from the test strip, with respect to the apex, a force acts upon the pressing mechanism away from the test strip. Thus, the position of the apex is such that the pressing mechanism, in the position corresponding to the apex, still does not lie against the thickest test strip to be measured. With such a construction, an especially dependable and simple operation of the pressing mechanism can be achieved because the range of movement of the pressing mechanism has a stable resting position.

In an especially preferred manner, the force transmission between the spring mechanism and the pressing mechanism is accomplished with the help of a lever mechanism which can be tilted about a lever axis and has two articulated connections for the articulation of the spring mechanism. This lever mechanism can be advantageously constructed in such a manner that a substantially uniform pressure of the piston upon the test strip is achieved, independently of the thickness thereof. By means of the arrangement of the articulated connections and of the articulation point of the preferably used tension or pressure spring on the lever mechanism, in each case relative to the axis of the lever mechanism and to the guide of the pressing mechanism, the leverages are fixed which determine the force transmission between the spring and the pressing mechanism. As will be explained in more detail hereinafter, these leverages change when the pressing mechanism assumes different positions in the case of the lying against the test strips of different thickness and, consequently, the corresponding rotation positions of the lever mechanism are also different. The positions of the pressing mechanism pressing against the test strip, which differ according to the thickness of the test strip, result, on the other hand, in automatically different deflections of the spring and thus in different spring forces. According to the present invention, the spring ratings, on the one hand, and the dimensioning of the mentioned constructional parts, on the other hand, are such that the mentioned leverages and the force of the spring change substantially reciprocally with respect to one another when the lever mechanism assumes different rotational positions in the pressing position in the case of various test strip thicknesses. By means of this preferred construction, a pressing force is achieved which is almost independent of the test strip thickness, a space-saving and economical method of construction thereby being possible at the same time.

According to a preferred embodiment of the present invention, the tilting range of the lever mechanism includes a position in which the axis of the fulcrum of the spring on the lever mechanism, the lever mechanism and the tilting axis of the spring on the side remote from the lever mechanism lie in one plane. In this position, the spring is stressed to a maximum, i.e. it is the apex of the tilting range. In the case of tilting the lever mechanism in both directions away from the apex, the spring is relieved whereby in practice, for pressing the test strip, the lever mechanism is by suitable means, for example the test strip itself or by an appropriate drive housed in the apparatus, moved from a position of the tilting range lying on one side of the apex against the force of the spring and towards the apex. When the apex is passed, the spring is again relieved so that the lever mechanism, on the other side of the tilting range, receives a tilting moment away from the apex due to the spring. In the case of this embodiment, too, there is also a clearance distance between the pressing mechanism and the strip in the apex position even for very thick test strips. The result of this is that the tilting movement of the lever mechanism after passing the apex, continues further, driven by the spring, until the mentioned clearance distance has been covered by the pressing mechanism. By means of this constructional measure, a substantial uniformity of the pressing force on test strips of different thickness and, simultaneously, a precise positioning of the test strips in a longitudinal direction is again achieved.

According to a further preferred embodiment, the lever mechanism can be operated by the test strip itself. In practice, the strip is inserted into the reception opening until it impinges against a corresponding stop surface of the lever mechanism. Upon further insertion of the test strip into the reception opening, the lever mechanism is preferably moved against the force of the spring towards the apex. It is especially advantageous when the arrangement of the test strip stop on the inner end of the reception opening and the leverages of the lever mechanism are dimensioned so that when the test strip is lying against the stop, the lever mechanism is tilted outwardly over the apex of the tilting range. The result of this is that the tilting movement of the lever mechanism, driven by the force of the spring, automatically runs further when the introduction of the test strip into the reception opening is finished and the test strip lies against the stop. The introduced test strip is still free, at this moment, because of the above-mentioned clearance, whereas the lever mechanism undergoes a rapid snapping movement which ends when the pressing mechanism lies against the test strip. The main advantage of such a form of construction is that the test strip can be introduced especially easily into the apparatus, no special drive for the pressing mechanism of the test strip is necessary and the test strip is very precisely fixed even in its longitudinal position.

The lever mechanism is preferably constructed as a cam plate. The pressing mechanism can, in particular, be constructed as a double-jointed, suspended pressing plate or as a laterally guided piston.

A further advantageous embodiment of the present invention serves for the return of the pressing mechanism from the pressing position into the resting position. According to this embodiment, the housing can be moved longitudinally for the removal of the test strip. Upon moving the housing, the cam plate is, preferably via an additional cam, brought together with an appropriate positionally fixed constructional part of the measuring apparatus, for example a ratchet present in the path of movement of the mentioned cam, in such a manner that upon moving the housing counter to the direction of insertion of the test strip which is usually done upon pulling the housing of the positioning device out from the measuring apparatus, the cam plate is tilted back from the pressing position into the resting position. The embodiment permits an especially simple removal of the test strip from the measuring apparatus. A special advantage is obtained in the case of a combination with the mentioned operation of the cam plate by the test strip. Thus, in this case, the test strip is pushed a little outwardly by the cam plate over its stop surface into the reception opening so that it can subsequently be removed especially easily. The same advantage is also achieved when the cam plate is constructed so as to be tilted backwardly by means of an appropriate drive.

The present invention will now be described in more detail, with reference to the embodiments illustrated in the accompanying drawings, wherein:

DETAILED DESCRIPTION OF THE INVENTION

Figure 1:
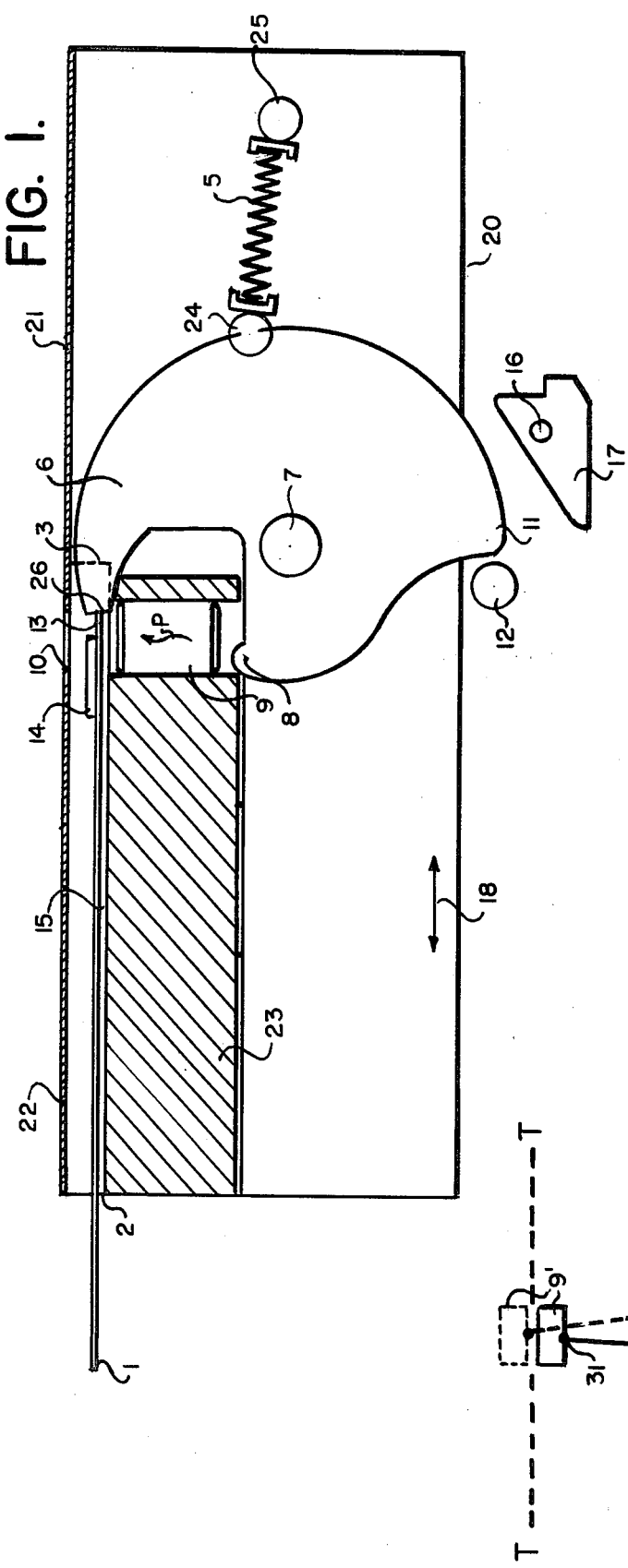
FIG. 1 is a schematic side view of a device according to the present invention, with the cover removed.

FIG. 1 of the accompanying drawings shows a device according to the present invention in which the pressing mechanism for the test strips is in the resting position. In a housing 20, there is arranged, near side 21 which faces the photoreceiver (not shown), a reception opening 2 for a test strip 1. The reception opening 2 is of approximately rectangular cross-section, the shape of which corresponds substantially to the shape of the test strips to be inserted. The opening is outwardly bounded by a wall 22, while on the inner side thereof there is provided an insert 23 which simultaneously receives a pressure piston 9 in its end lying in the middle of the housing 20. The wall 22 is provided with a window 10 in the range of which a test zone 14 of the test strip 1 is to lie when the test strip is fully inserted. For this positioning of the test strip 1, the inner end 13 of the reception opening 2 is provided with a stop 3 which extends on both sides of the cam plate 6, only the part lying behind the cam plate being indicated by a broken line. In a usual embodiment of the device, the stop 3 is about 6 mm. from the middle of the test zone 14, at which distance the test zone comes to lie directly below the window 10.

The cam plate 6 is rotatably fixed onto the housing 20 by an axis 7. The cam plate 6 has a cam 8 which engages directly on the piston 9. Furthermore, via an articulated joint 24, a pressure spring 5 is fixed onto the cam plate 6. The other end of the pressure spring 5 is attached in an articulated manner on a tilting axis 25 on the housing 20. The axis 7 of the cam plate 6 and the tilting axis 25 lie in the same plane.

The cam plate 6 is laterally, i.e. towards the test strip 1, provided with a contact surface 26 which, in the open position of the device, i.e. in the illustrated resting position, projects up to the window 10. During insertion of the test strip 1 into the opening 2, the end of the test strip comes to lie against the contact surface 26. Upon further insertion of the test strip 1 into the opening 2, the cam plate 6 is rotated clockwise about its axis 7. In the case of this rotational movement, the spring 5 is first tensioned until the axis 7, the articulated joint 24 and the tilting axis 25 lie on one line in the side view illustrated in FIG. 1. Regarded spatially, the three axes 7, 24 and 25, which run substantially parallel to one another, then lie in one plane. This position is the apex of the tilting movement of the cam plate. Instead of the illustrated pressure spring, there can, of course, also be used a tension spring which then, for example, in the case of a construction which otherwise corresponds to the illustrated embodiment, would have to have its tilting axis 25 to the left of the articulated joint 24 in FIG. 1.

During the above-described first part of the rotating movement of the cam plate, the cam 8 has passed through a clearance possibly present between it and the lower side of the pressing piston 9 and now lies on the lower side of the piston 9. The piston 9 has also already been passed upwardly somewhat but has not yet passed into the region of the reception opening. When the cam plate 6 is at the apex, the contact surface 26 still projects a little to the left in FIG. 1 with regard to the stop 3. Upon further insertion of the test strip, the innermost end of the test strip comes to lie against the stop 3, which determines its longitudinal position. At this moment, the cam plate 6 has passed the apex and, driven by the force of the spring 5, undergoes a snapping movement in which the test strip is firmly gripped. The height of the piston 9 and the leverages of the cam plate are such that the piston, even in the case of very thick test strips 1, does not immediately lie against the rear side of the test strip. On the contrary, the cam plate 6, before coming to lie against the test strip, is to be tilted to such an extent that the force of the spring transmitted to the piston 9 by the lever transmission, which is described hereinafter in more detail, suffices reliably to hold the test strip firmly.

The housing 20 of the device according to the present invention is preferably mounted in a sliding mounting (not shown in FIG. 1) so as to be movable in the longitudinal direction indicated by the double arrow 18. For measuring, the housing 20 is moved to the right in FIG. 1, a cam 11 of the cam plate 6 thereby slipping over a ratchet 17 which is tiltable about an axis 16 and is thereby tilted clockwise. Thereafter, the ratchet 17 drops back into the position illustrated in FIG. 1 and is secured against rotation in the counterclockwise direction. For the ejection of a test strip 1, the whole housing is moved towards the left in FIG. 1 until the cam 11 of the cam plate engages with the right edge of the ratchet 17. Upon further movement of the housing 20 to the left, the cam plate 6 is thereby tilted back counterclockwise, the pressing piston 9 thereby being released from the rear side 15 of the test strip 1 and the test strip is pushed to the left by the contact surface 26 outwardly of the reception opening 2. Thereafter, the test strip can be removed particularly easily from the measurement device.

Upon tilting the cam plate, the cam 11 also operates a switch 12 for switching the optical measuring device on and off.

Figure 2:
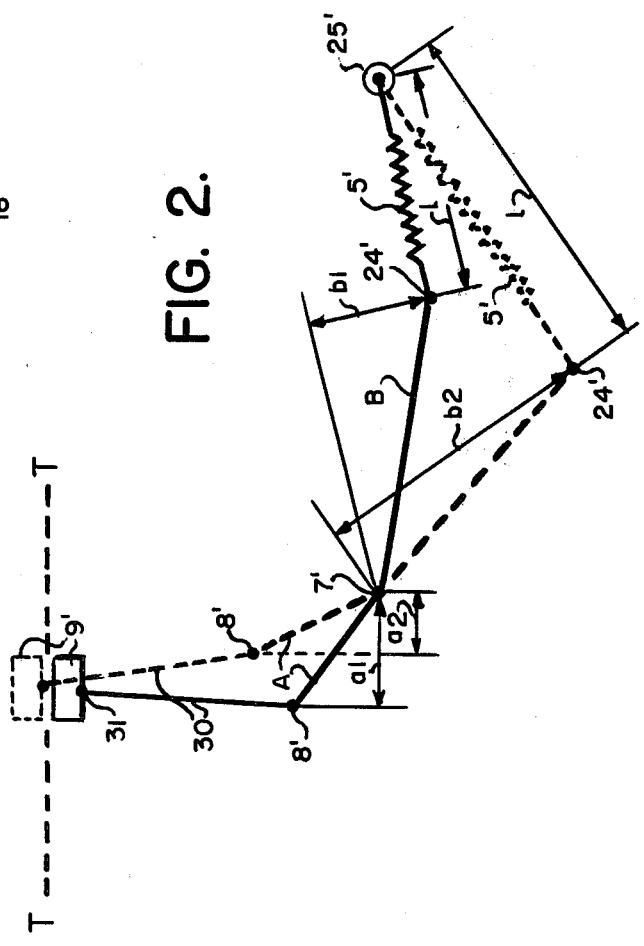
FIG. 2 is a geometrical representation of the principle for explaining the prevailing leverages and measurements in various positions of the cam plate of FIG. 1.

FIG. 2 shows, in geometric schematic representation, the lever action upon the cam plate in two different cam plate positions, the first position being illustrated by an unbroken line and the second position by a broken line. In the first position, the cam plate has, in its snapping movement into the pressing position, just passed the apex and the second position corresponds to the pressing position in the case of a comparatively thin test strip. FIG. 2 is intended to clarify the principle of the operating leverages and is not to be regarded as being limited in any way.

Generally speaking, the cam plate represents a lever mechanism with two levers A and B, a lever axis 7' being between the two levers. The fulcrum 8' is associated with the operating cam 8, this fulcrum 8' transmitting the movement, via transmission rod 30 and coupling 31, to a piston 9' which, in this case, is constructed as a pressure plate and guided in a vertical direction. The line T—T marks the position of the lower side of the thickest test strip to be measured, in the state of being pressed against the window of the optical system.

Spring 5' is attached to the articulated joint 24', the other end of the spring 5' being tiltably mounted on tilting axis 25'.

For the calculation of the force acting on the pressure plate 9', the effective lever lengths of the levers A and B must be used, these being the projections of these levers at right-angles to the acting forces. In FIG. 2, these lever lengths are indicated by the following references:

b1: effective force lever B in the first position
b2: effective force lever B in the second position
a1: effective force lever A in the first position
a2: effective force lever A in the second position The force F emanating from the spring 5' is the product of the spring path s and the spring rating c. The spring is prestressed and the spring path s is calculated as the difference of the length of the spring in the unstressed state Lo and the spring length in the particular position 1.

As can be seen from FIG. 2, the lever lengths a and b and the spring lengths 1 are different depending upon the position of the cam plate or of the here schematically illustrated lever mechanism. After passing the apex, the lever length b increases in a clockwise direction, whereas the lever length a decreases. In this way, the leverage of the spring force on the pressing plate 9' becomes ever greater. At the same time, the force of the spring decreases because of its increasing elongation. The dimensions of the device according to the present invention can now be made such that these two counter effects are almost compensated by each other and thus, over a certain tilting range, the force acting on the pressing plate and thus on the test strip remains almost constant. For a spring with an untensioned length Lo of 18.3 mm. and a spring rating of 0.01 Newton (N) mm., the following Table shows, by way of example, this advantageous result:

TABLE

| test strip thickness in mm. | spring length l in mm. | spring path s = Lo − l in mm. | spring force F = c × s N | a mm. | b mm. | pressure on the test strip $P = \frac{F \cdot b}{a}$ N |
|---|---|---|---|---|---|---|
| 0.3 | 12.44 | 5.86 | 0.586 | 5.1 | 11.8 | 1.3558 |
| 0.4 | 12.22 | 6.08 | 0.608 | 5.2 | 11.6 | 1.3563 |
| 0.5 | 11.98 | 6.32 | 0.632 | 5.25 | 11.5 | 1.3843 |
| 0.6 | 11.78 | 6.52 | 0.652 | 5.3 | 11.3 | 1.3901 |
| 0.7 | 11.58 | 6.72 | 0.672 | 5.35 | 11 | 1.3816 |
| 0.8 | 11.3 | 7.00 | 0.700 | 5.4 | 10.7 | 1.387 |
| 0.9 | 11.1 | 7.2 | 0.720 | 5.45 | 10.4 | 1.3739 |
| 1.0 | 10.9 | 7.4 | 0.740 | 5.5 | 10.2 | 1.3723 |
| 1.1 | 10.75 | 7.55 | 0.755 | 5.55 | 9.9 | 1.3467 |

As can be seen from the above Table, in the case of a test strip thickness of 0.3 mm., the spring force is 0.586 N and, in the case of a test strip thickness of 1.1 mm., is 0.755 N. Thus, in the case of a very thick test strip, the spring force is almost 30% greater than in the case of a very thin test strip. On the other hand, because of the reciprocal change of the leverages, the pressure on the test strips changes to a far lesser extend. In the case of the embodiment illustrated in the Table, in the case of average test strip thicknesses, it achieves a maximum value which, however, only differs by less than 4% from the smallest value. Whereas the first-mentioned force difference, as experience demonstrates, leads to a considerable inexactitude of the measurement result in the case of optical evaluation of the test strip, the measurement result is only very slightly affected by the remaining small pressure differences in the case of the apparatus according to the present invention.

Figure 3A:
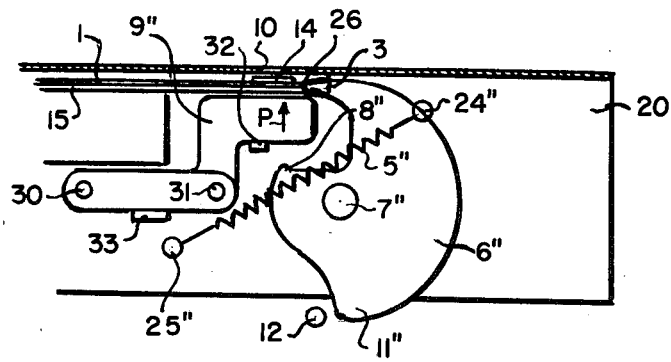
FIGS. 3a to 3c are schematic side views of a further embodiment of the present invention, showing three different positions of the cam plate and of the pressing mechanism.
Figure 3B:
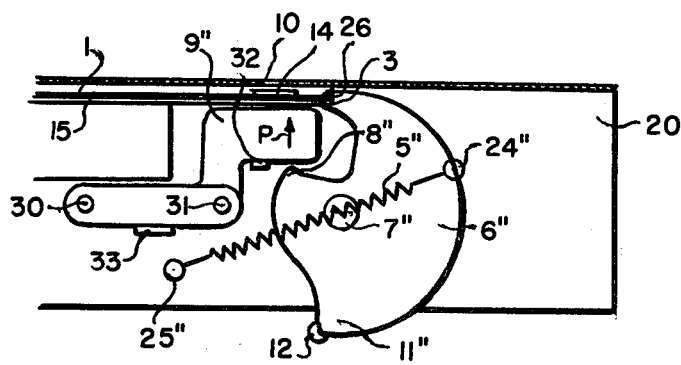
Figure 3C:
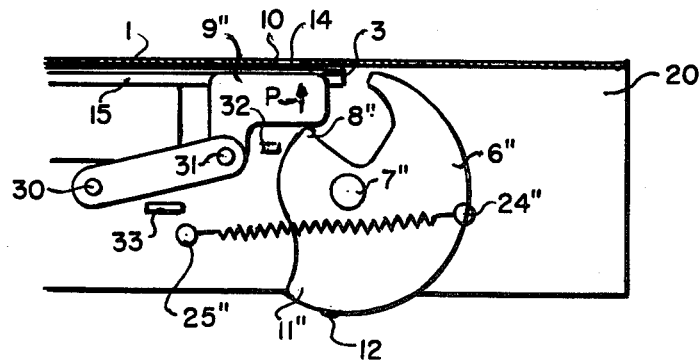

The preferred embodiment of the present invention illustrated in FIGS. 3a to 3c of the accompanying drawings differs from the embodiment illustrated in FIG. 1 of the accompanying drawings especially in that the pressure device is constructed as a double-jointed suspended pressing plate 9″ instead of as a laterally guided piston 9. Otherwise, the same reference numerals indicate the corresponding parts of the embodiment of FIG. 1. Constructional parts which are changes in comparison with the embodiment of FIG. 1 or which are arranged in a different manner are additionally indicated by a double prime. These are, in particular, the cam plate 6″, the axis 7″, the pressing plate 9″, the additional cam 11″, a spring mechanism constructed in this case as a tension spring 5" with a cam disc side-articulated joint 24" and a tilting mount 25" and a cam 8" which acts as an articulated joint between the cam plate 6" and the pressing plate 9".

As can be seen from FIGS. 3a to 3c, the pressing plate 9" is double-jointedly suspended by two joints 30 and 31 so that it lies against the rear side of the test strip and, consequently, a precisely vertical action of force of the pressing plate on the test strip 1 is guaranteed which, in turn, lies against the window 10. For holding the pressing plate 9" in the resting position, two mountings 32 and 33 are provided which are attached to the housing 20 in an appropriate manner.

FIG. 3a shows the resting position of the pressing device, the test strip 1 just having been inserted into the reception opening of the apparatus to such an extent that it lies against the contact surface 26 of the cam plate 6". In FIG. 3b, the cam plate 6" is present just at the apex of its tilting movement, the spring 5" being tensioned to a maximum, the axis of the articulated joint 24", the lever axis 7" and the axis of the tilting mount 25" lying on one plane. At this moment, the test strip 1 is in a position just short of the stop 3, which is substantially obscured in FIG. 3b. When the test strip is further moved in the insertion direction, then it finally impinges against the stop 3 in the manner illustrated in FIG. 3c. Due to the force of the spring 5", the cam plate is moved into the pressing position, illustrated in FIG. 3c, in which the test strip is dependably and exactly positioned.

What is claimed is:

1. A device for positioning and firmly holding a medical test strip, said device comprising: a housing having a strip reception opening, means forming a stop at the inner end of the opening for the inserted end of the test strip and a window positioned to be opposite a predetermined test zone of the test strip when inserted into the reception opening and abutting against the stop; means for pressing substantially at right-angles on the rear side of the test-strip strip towards said window, the pressing means being movable between a rest position wherein it is spaced from the rear side of the inserted test strip and a pressing position in which it presses the test strip against the window; and means responsive to the insertion of a test strip for moving the pressing means from the rest to the pressing position and for applying a pressing force which is substantially uniform in the positions corresponding to various thicknesses of insertable test strips.

2. The device according to claim 1, wherein the moving means includes an actuating member disposed in the region of the stop to initiate movement of the pressing means into the pressing position.

3. The device according to claim 2, wherein the moving means comprises a spring mechanism in positive connection with the pressing means and wherein the transmission relationship of the force transmission and the force of the spring mechanism changes substantially reciprocally in the movement range corresponding to a given range of test strip thicknesses.

4. The device according to claim 3, wherein the driving movement of the moving means on the pressing means includes a first range in which the force acts in the direction of the test strip and a second range in which the force acts away from the test strip wherein the pressing means at the apex separating the two ranges is spaced apart from the preselected thickest test strip to be measured.

5. The device according to claim 3, wherein the force transmission between the spring mechanism and the pressing means includes a lever mechanism tiltable about a lever axis, said lever mechanism having a first articulated joint for the articulation of the pressing means and a second articulated joint for the articulation of the spring mechanism.

6. The device according to claim 5, wherein the spring mechanism comprises a spring which is articulated from the end of the spring remote from the lever mechanism in a tilting mount, the spring being prestressed and the arrangement of the articulated joints on the lever mechanism, the spring prestressing and the spring constants being such that the leverage, on the one hand, and the spring force, on the other hand, change substantially reciprocally in the tilting range of the lever mechanism corresponding to the thickness of the different test strips to be measured.

7. The device according to claim 6, wherein the operational tilting range of the lever mechanism has an apex in which the axis of the second articulated joint, the lever axis and the axis of the tilting mount of the spring mechanism, which run substantially parallel to one another lie in one plane and in which the spring mechanism is tensioned to a maximum.

8. The device according to claim 5, wherein the lever mechanism includes the actuating member which comprises a contact surface for the test strip through which the lever mechanism is tiltable by the test strip and wherein the lever mechanism is dimensioned such that when a test strip is lying against the stop the lever mechanism is tilted over the apex of the tilting range.

9. The device according to claim 5, wherein the pressing means comprises a doubly articulated, suspended pressing plate and the lever mechanism comprises a cam plate and wherein the articulated joint between the pressing plate and the cam plate comprises a cam on the cam plate cooperating with the rear side of the pressing plate.

10. The device according to claim 5, wherein the pressing means comprises a laterally guided piston and the lever mechanism comprises a cam plate and wherein the piston is operable by a cam on the cam plate.

11. The device according to claim 9 or 10, wherein the device is used in a measuring apparatus and further comprising a switch for the provision of energy for the measuring device and a cam on the cam plate for actuating the switch.

12. The device according to claim 5, wherein the cam plate includes means responsive to the lateral movement of the housing from a measuring apparatus to effect movement of the pressing means from the pressing to the rest position so that the test strip is freed.

* * * * *